(12) United States Patent
Waluszko (10) Patent No.: US 6,670,619 B2
(45) Date of Patent: Dec. 30, 2003

(54) TRANSILLUMINATOR

(76) Inventor: Alex Waluszko, 2066 W. 11th St., Upland, CA (US) 91786

( * ) Notice: Subject to any disclaimer, the term of this patent is extended or adjusted under 35 U.S.C. 154(b) by 0 days.

(21) Appl. No.: 10/015,427

(22) Filed: Dec. 12, 2001

(65) Prior Publication Data

US 2003/0107010 A1 Jun. 12, 2003

(51) Int. Cl.[7] .............. G01J 1/42; G01N 21/00; A61N 5/00; G21G 5/00; G21G 4/00
(52) U.S. Cl. .............. 250/492.1; 250/365; 250/372; 250/454.1; 250/455.1; 250/493.1; 250/494.1; 250/504 R; 250/505.1
(58) Field of Search .............. 250/492.1, 504 R, 250/365, 494.1, 372, 454.1, 455.1, 493.1, 505.1; 355/113

(56) References Cited

U.S. PATENT DOCUMENTS

| | | | | |
|---|---|---|---|---|
| 5,175,437 A | * | 12/1992 | Waluszko | 250/504 R |
| 5,387,801 A | * | 2/1995 | Gonzalez et al. | 250/504 R |
| 5,670,786 A | * | 9/1997 | Meyer et al. | 250/494.1 |
| 5,736,744 A | * | 4/1998 | Johannsen et al. | 250/505.1 |
| 5,737,065 A | * | 4/1998 | Hansen | 355/113 |

* cited by examiner

Primary Examiner—John R. Lee
Assistant Examiner—Mary El-Shammaa
(74) Attorney, Agent, or Firm—J. E. Brunton, Esquire (57) ABSTRACT

An apparatus for expeditiously irradiating an object with ultraviolet radiation at a selected UV wavelength. The apparatus includes a plurality of ultraviolet sources, each emitting radiation at a first wave length. The UV sources are mounted within a housing that also supports one or more conversion plates that can be interposed between the UV sources and the specimen and function to convert the UV to a second wavelength.

4 Claims, 8 Drawing Sheets

TRANSILLUMINATOR

BACKGROUND OF THE INVENTION

1. Field of the Invention

The present invention relates generally to radiation devices. More particularly, the invention concerns an apparatus for irradiating various articles with ultraviolet radiation from a radiation source such as a plurality of ultra-violet lamps.

2. Discussion of Prior Art

Ultra-violet radiation is widely used in industry and science for sterilization through inactivation of microorganisms, for inducing and promoting various types of photochemical reactions and for controllably exposing various types of photosensitive materials. By way of example, U.S. Pat. No. 5,175,437 issued to the present inventor describes an apparatus for irradiating an object such as a specimen of material with ultraviolet radiation at a selected long, short or mid-wave length. Similarly, U.S. Pat. No. 3,936,186 issued to Boland et al discloses an apparatus for exposing diazo printing plates and the like of the character that are used in the graphic arts field. In like manner, U.S. Pat. No. 5,288,647 issued Zimlich, Jr. et al relates to a method by which polynucleotide specimens can be irradiated particularly for the purpose of fixing them to a substrate.

Ultraviolet light (UV), which is electromagnetic radiation in the region of the spectrum located between X-rays and visible light, is typically divided into three principal ranges, namely long wave, mid-range, and short wave. For each of these UV ranges specific applications have been developed.

As a general rule, the desired ultraviolet wavelength is obtained from a fluorescent style tube that is an electric discharge device that uses a low-pressure mercury vapor arc to generate ultraviolet energy. The ultraviolet energy released in typical, commercially available fluorescent tubes is primarily at the wavelength of about 254 nanometers. The fluorescent tubes can be modified to release other ultraviolet wavelengths by the use of phosphors, which have the ability to absorb the ultraviolet energy and re-radiate it in other wavelengths. For example, long wave ultraviolet of about 365 nanometers and mid-range ultraviolet of about 300 nanometers are created by coating the inside of the fluorescent tubes with the proper phosphors which convert the short wave ultraviolet.

In the past ultraviolet irradiation of selected articles has been accomplished using a single UV range fluorescent tube mounted within a suitable enclosure. In order to eliminate white light generated by the UV tube, some prior art devices make use of a UV transmitting light blocking filter that is typically mounted in front of the UV tube.

In the past, when it was desired to obtain two UV wave lengths from the radiation device, two UV tubes emitting two levels of UV radiation were mounted side by side within the device, and an appropriate filter was placed in front of each tube.

In the apparatus disclosed in the previously identified U.S. Pat. No. 5,175,347 issued to the present inventor, a different and novel technique was used to irradiating an object, with ultraviolet radiation at a selected long, short or mid-wave length. More particularly, in this prior art apparatus, a plurality of ultraviolet sources, each emitting radiation at a different wave length, were mounted within a rotatable array so that a selected one of the sources could be moved into alignment with the specimen and automatically energized by merely rotating the array.

As will be better understood from the discussion that follows, the present invention enables the controlled irradiation of a specimen with UV at selected wavelengths through the use of a novel wavelength conversion means that can be interposed between the UV source and the specimen.

SUMMARY OF THE INVENTION

It is an object of the present invention to provide an apparatus for expeditiously irradiating an object with ultraviolet radiation at a selected UV wavelength.

More particularly, the apparatus of the invention comprises a plurality of ultraviolet sources, each emitting radiation at a first wave length. The UV sources are mounted within a housing that also supports a novel conversion plate that can be interposed between the UV sources and the specimen and functions to convert the UV to a second wavelength.

Another object of the invention is to provide an apparatus of the aforementioned character in which the conversion plate is slidably carried by the housing.

Another object of the invention is to provide an apparatus as described in the preceding paragraphs in which the specimen can be irradiated with ultraviolet radiation at a selected wave length between about 254 nanometers and about 365 nanometers.

Still another object of the invention is to provide an apparatus of the class described, which includes strategically located reflectors for reflecting the ultraviolet radiation in a direction toward the specimen. Another object of the invention is to provide an apparatus as described in the preceding paragraphs in which a filter for blocking white light from the UV sources is interposed between the specimen and the UV sources.

Yet another object of the invention is to provide an apparatus of the character described which is of a simple, compact construction that is easy to use and can be inexpensively manufactured.

DESCRIPTION OF THE INVENTION

Referring to the drawings and particularly to FIGS. 1 through 9, one form of the irradiation apparatus of the present invention is there illustrated and generally designated by the numeral 12. The apparatus of this form of the invention comprises a housing 14 having interconnected top, bottom and sidewalls 16, 18, and 20 respectively that define an internal chamber 22. Carried by top wall 16 is filter means filter for blocking white light from the UV sources 24 that are disposed within internal chamber 22. The filter means here comprises a UV transmitting light blocking filter 26. Filter 26 is adapted to carry an article, such as a specimen that is to be irradiated as, for example, a ploynucleocide. In the present form of the invention, filter 26 blocks white light.

Figure 1:
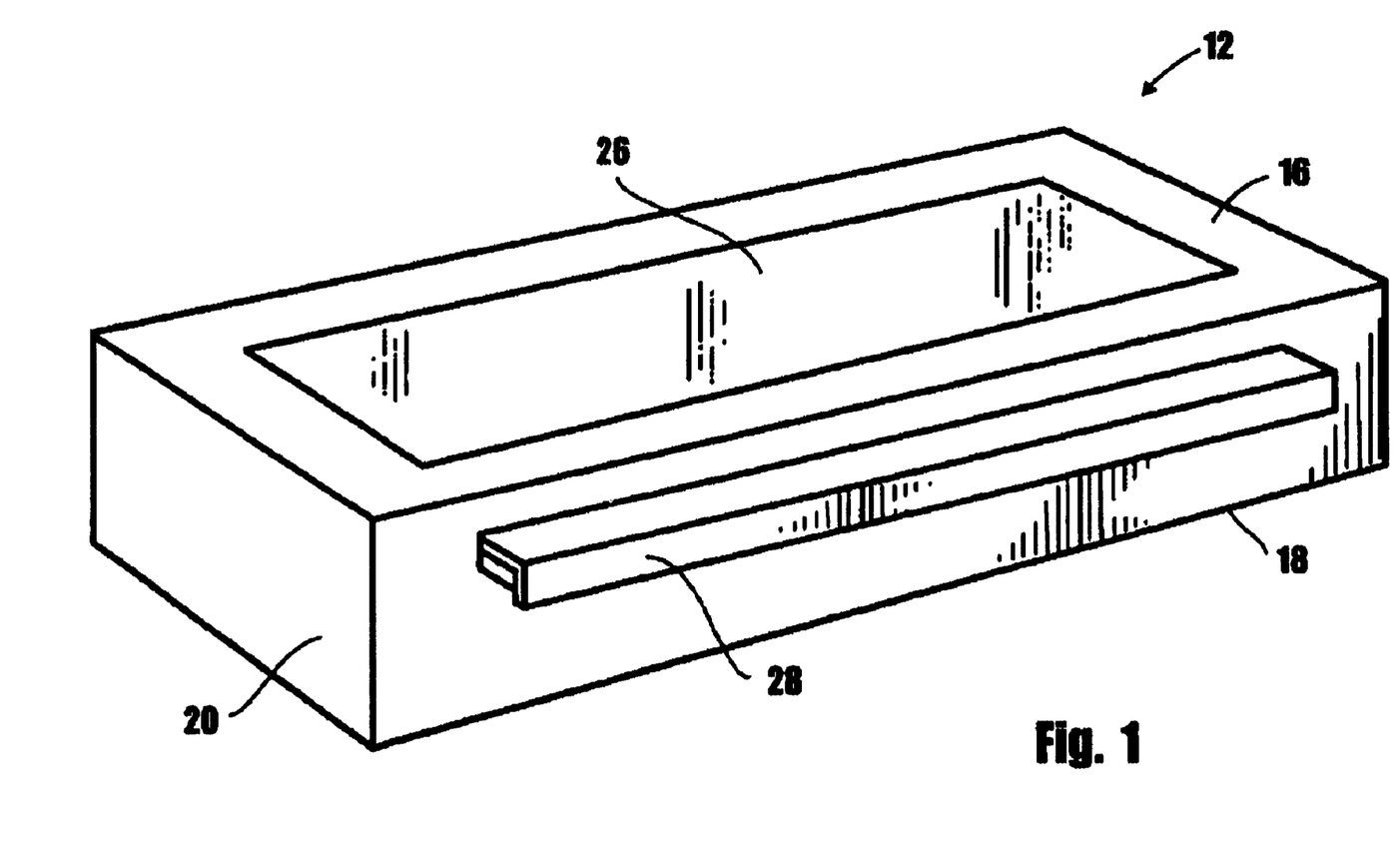
FIG. 1 is a generally perspective view of one form of the apparatus of the invention for irradiating an object with ultraviolet radiation.
Figure 2:
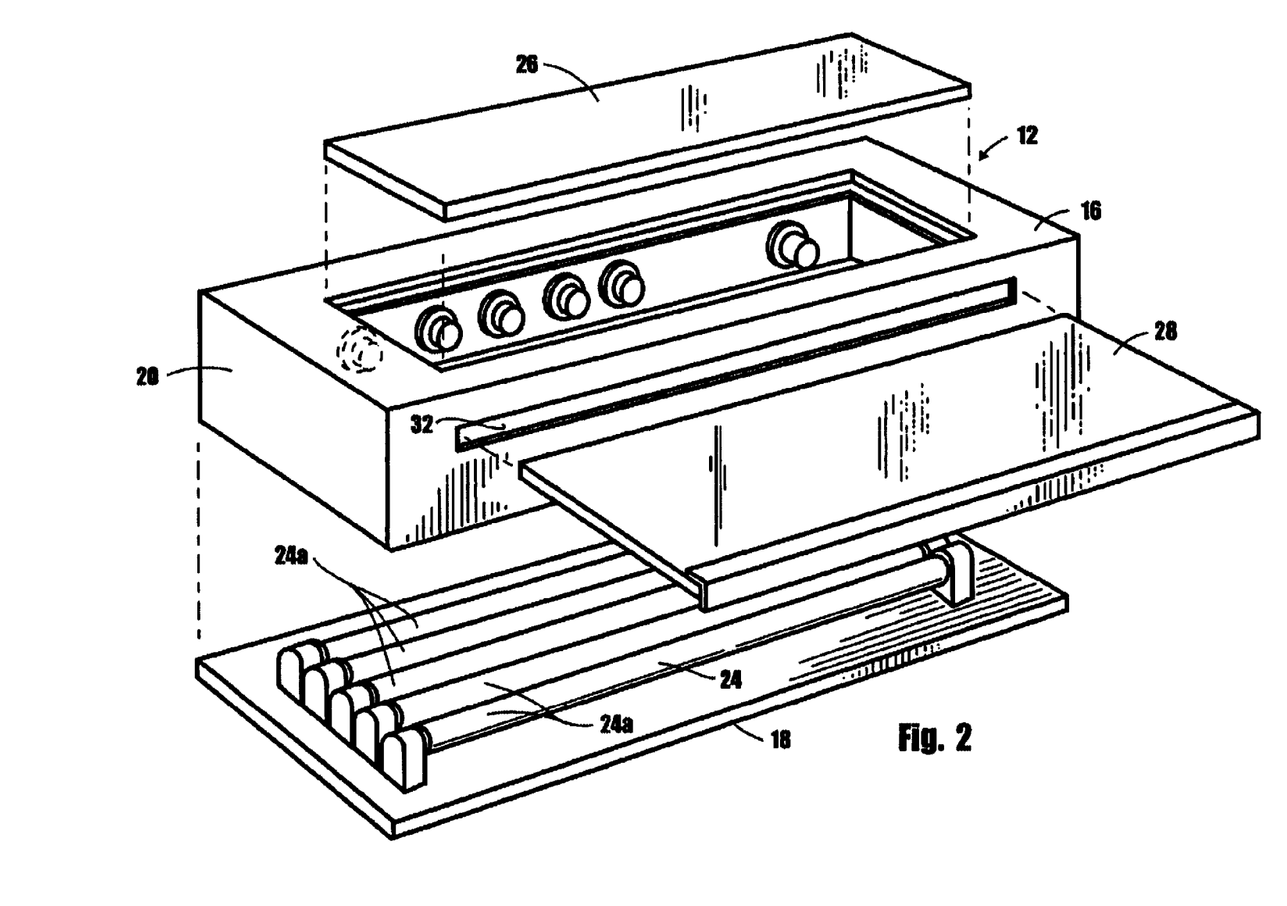
FIG. 2 is a generally perspective, exploded view of the apparatus shown in FIG. 1.
Figure 3:
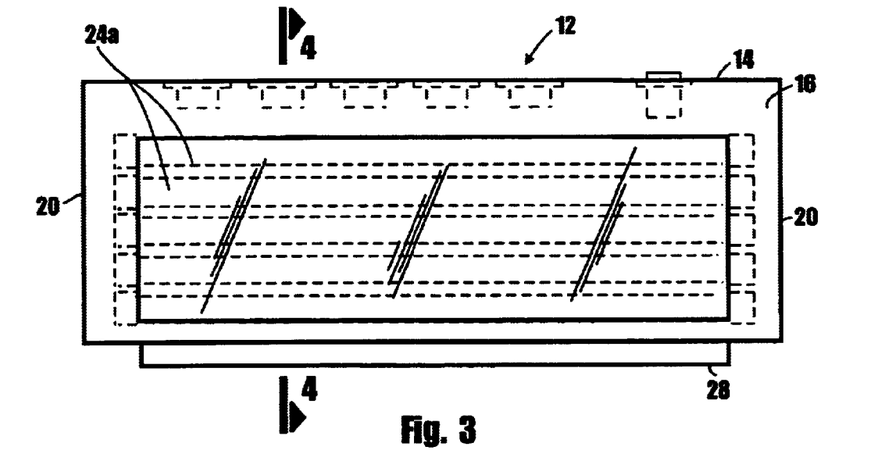
FIG. 3 is a top plan view of the apparatus shown in FIG. 1.
Figure 4:
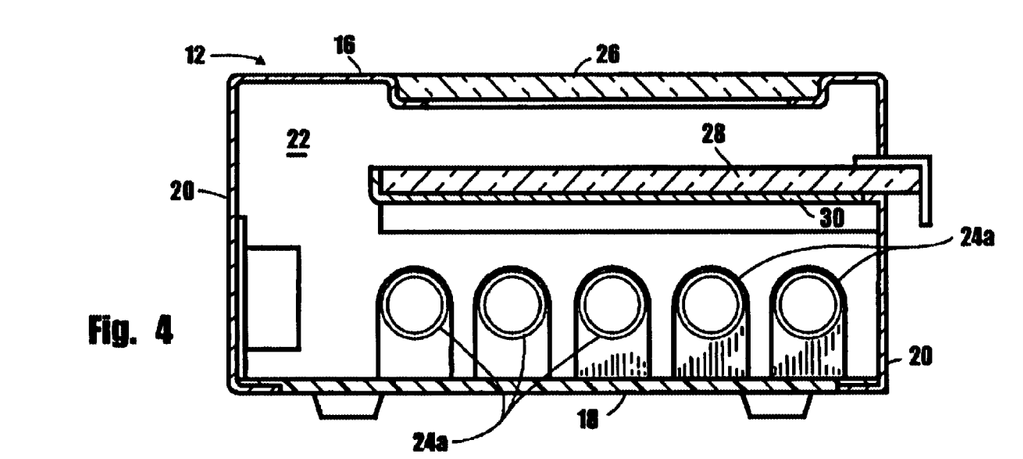
FIG. 4 is a cross-sectional to take along lines 4—4 FIG. 3.
Figure 5:
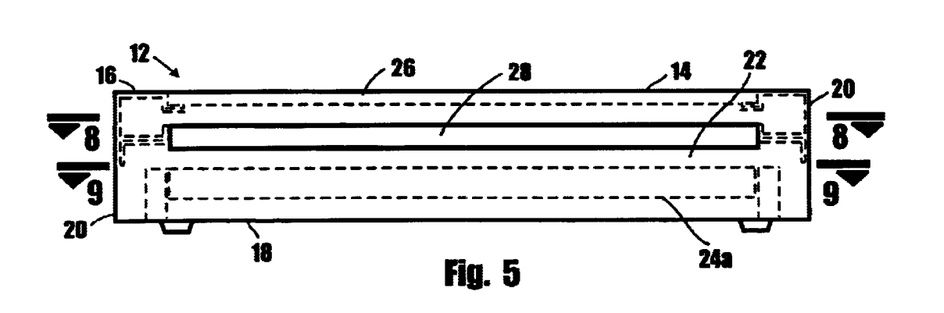
FIG. 5 is a side elevational view of the apparatus shown in FIG. 1.
Figure 6:
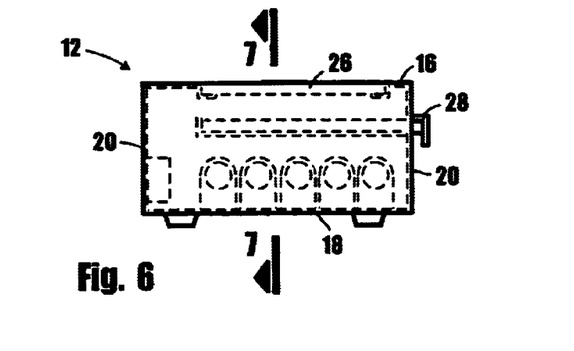
FIG. 6 is an end view of the apparatus shown in FIG. 1.
Figure 7:
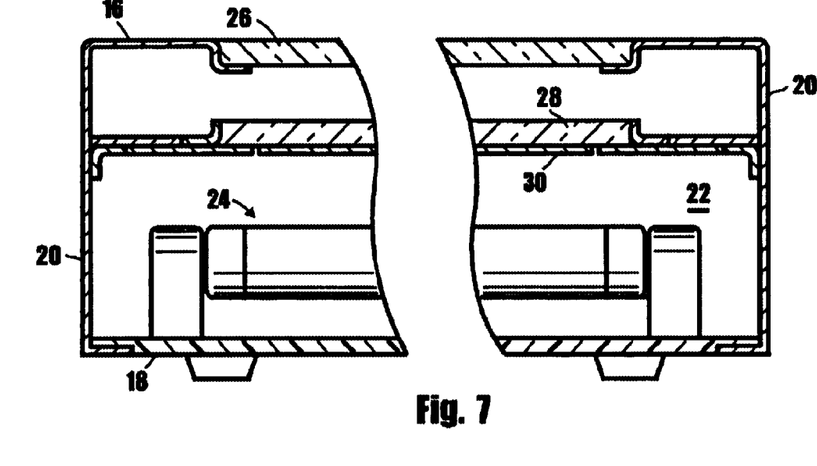
FIG. 7 is a cross-sectional view taken along lines 7—7 of FIG. 6.
Figure 8:
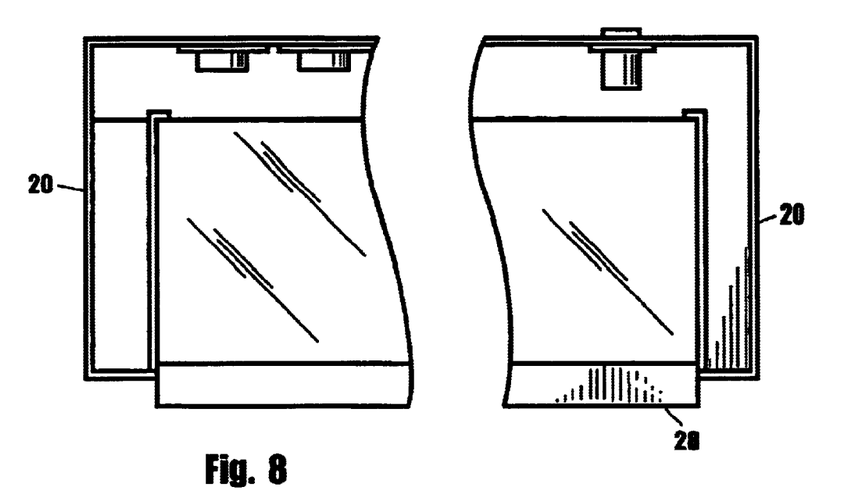
FIG. 8 is a cross-sectional view taken along lines 8—8 of FIG. 5.
Figure 9:
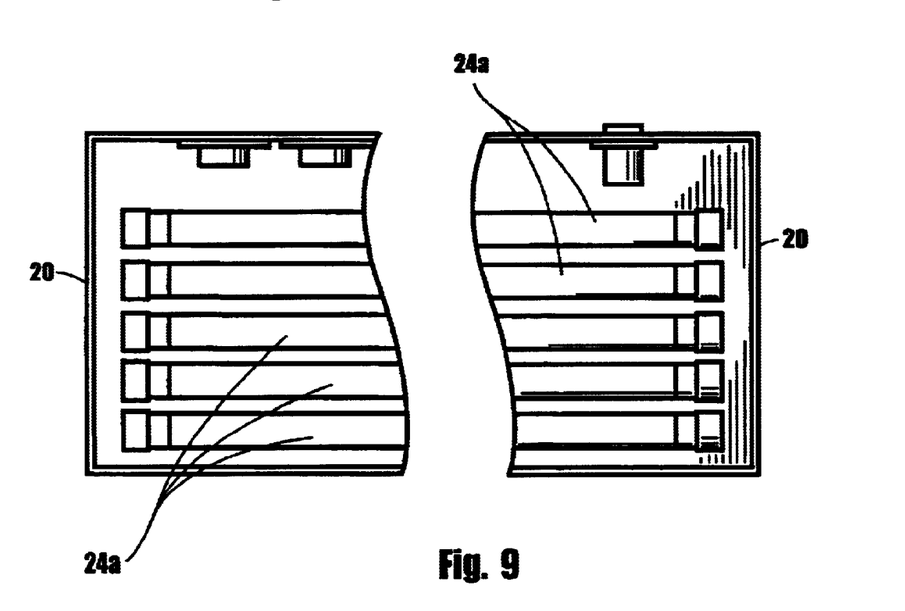
FIG. 9 is a cross-sectional view taken along lines 9—9 in FIG. 5.
Figure 10:
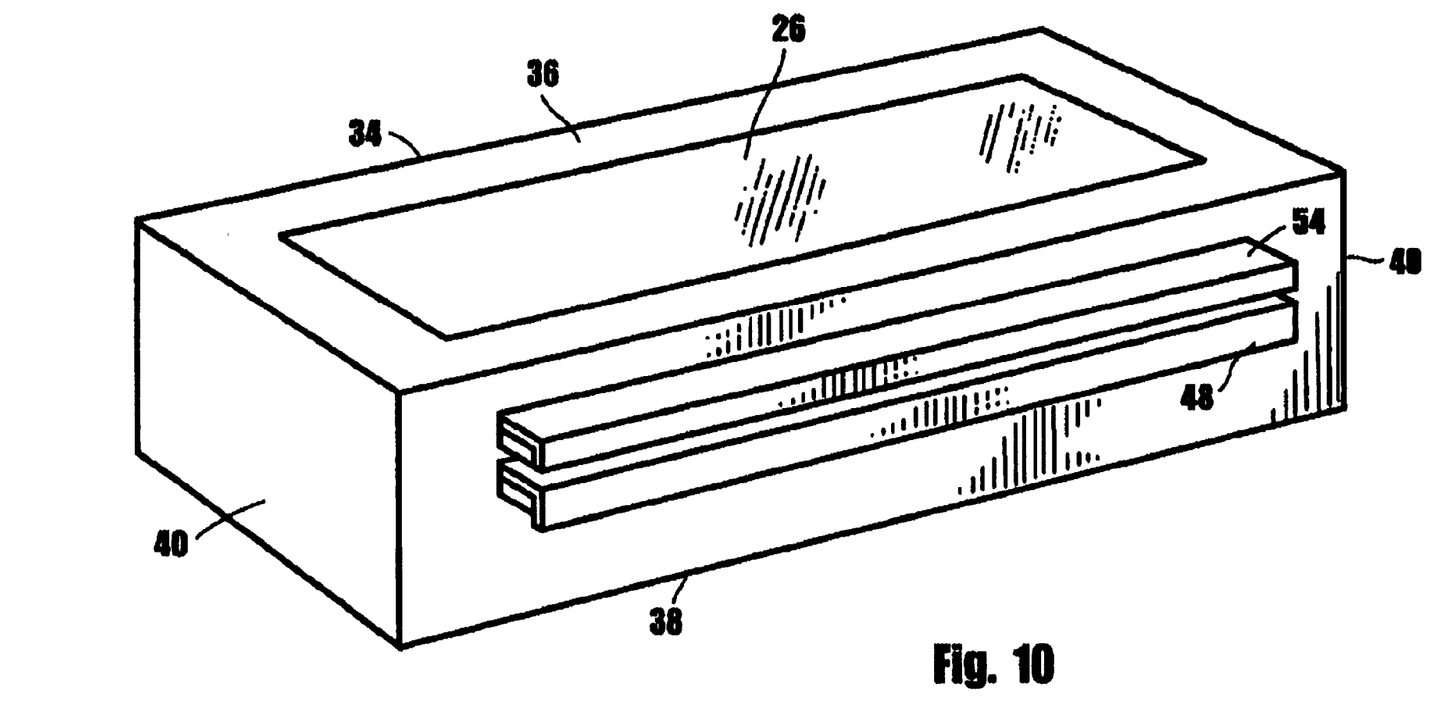
FIG. 10 is a generally perspective view of an alternate form of the apparatus of the invention.

As best seen in FIG. 2, the UV sources here comprises a plurality of spaced-apart, ultraviolet-light-emitting lamps 24a that emit UV radiation at a first wavelength of, for example, 254 nanometers. Positioned between the array of lamps 24a and filter 26 is the highly novel first wavelength conversion means of the invention which is adapted to convert the UV radiation at the first wavelength to UV radiation at a second wavelength of, for example, 365 nanometers. This first wavelength conversion means here comprises a conversion plate 28 that is removably carried by housing 14 at a location intermediate filter 26 and UV source 24. More particularly, plate 28 is provided with a wave shifting phosphor coating 30 (FIGS. 4 and 7) and is slidably movable within a slot 32 formed in housing. With this construction, plate 28 can be readily removed from the housing and replaced with another plate if desired. As is well known in the art, phosphors are compounds that are capable of emitting useful quantities of radiation in the visible and/or ultraviolet spectrums upon excitation of the material by an external energy source. Due to this property, phosphor compounds have long been utilized in cathode ray tube (CRT) screens for televisions and similar devices. Typically, inorganic phosphor compounds include a host material doped with a small amount of an activator ion. In recent years, phosphor compounds, including phosphors in particulate form, have been used in display devices, decorations, cathode ray tubes, and fluorescent lighting fixtures. Luminescence or light emission by phosphor particles may be stimulated by application of heat (thermoluminescence), light (photoluminescence), high energy radiation (e.g., x-rays or e-beams), or electric fields (electroluminescence). A comprehensive discussion of various types of phosphors can be found in U.S. Pat. No. 6,193,908 issued to Hampden-Smith et al.

Turning to FIGS. 10 through 13, an alternate form of transilluminator of the invention is there shown. This form of the invention is similar in many respects to that shown in FIGS. 1 through 9 and like numerals are used in FIGS. 10 through 13 to identify like components. This alternate form of the invention comprises a housing 34 having interconnected top, bottom and sidewalls 36, 38, and 40 respectively that define an internal chamber 42. Carried by top wall 36 is filter means filter for blocking white light from the UV sources 24 that are disposed within internal chamber 42. The filter means here comprises a UV transmitting light blocking filter 26. As before, filter 26 is adapted to carry an article, such as a specimen that is to be irradiated.

Figure 11:
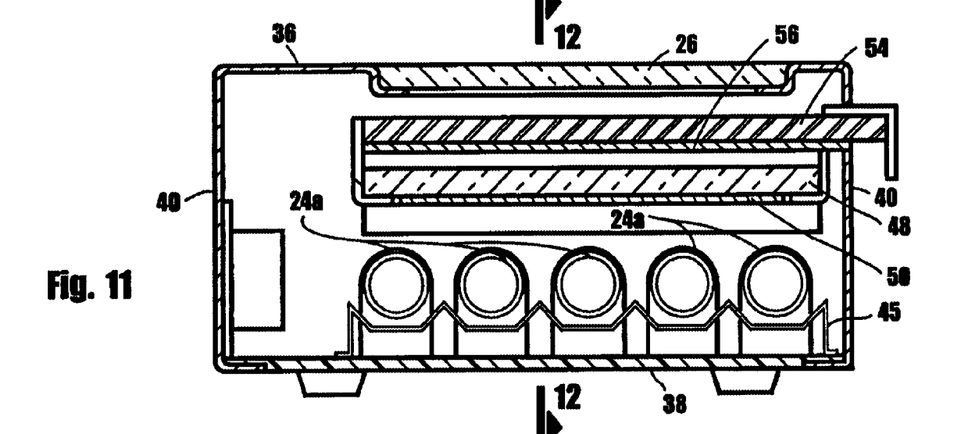
FIG. 11 is a transverse, cross-sectional view of the form of the apparatus shown in FIG. 10.
Figure 12:
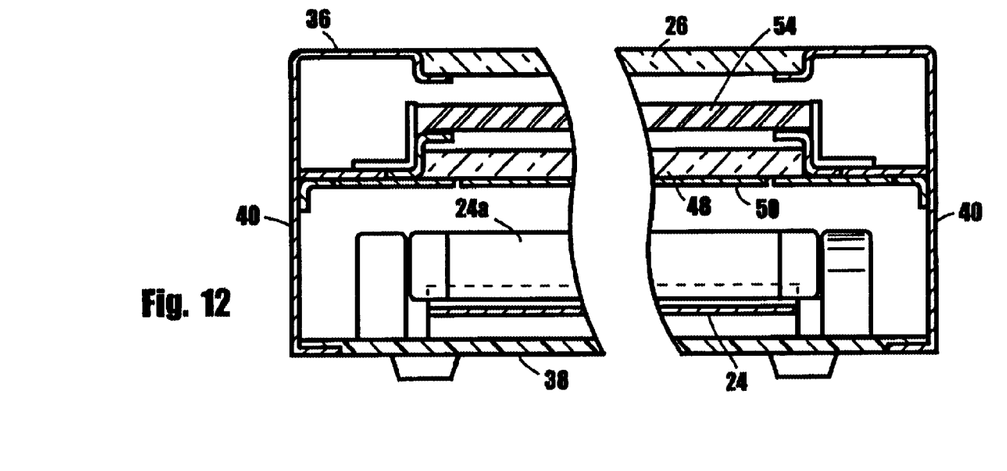
FIG. 12 is a cross-sectional view taken along lines 12—12 FIG. 11.
Figure 13:
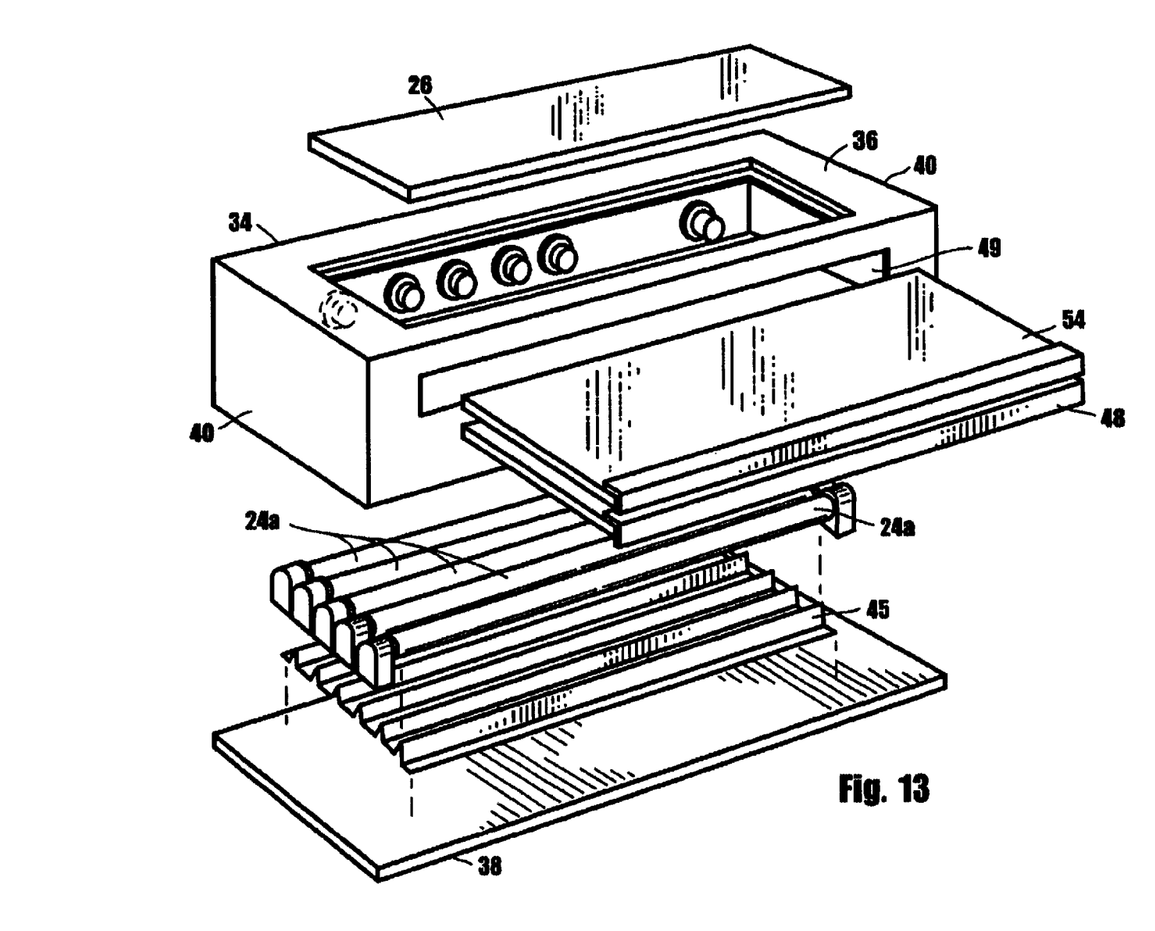
FIG. 13 is a generally perspective, exploded view of the alternate form of the apparatus shown in FIG. 10.

As best seen in FIG. 11, the UV sources here comprises a plurality of spaced-apart, ultraviolet-light-emitting lamps 24a that emit UV radiation at a first wavelength of, for example, 254 nanometers. Lamps 24a are here positioned over a corrugated reflector 45. Positioned between the array of lamps 24a and filter 26 are first and second wavelength conversion means which are adapted to convert the UV radiation at the first wavelength to UV radiation at a second wavelength of, for example, 300 nanometers and then to UV radiation at a third wavelength of, for example, 365 nanometers. This first wavelength conversion means here comprises a first conversion plate 48 that is removably carried by housing 34 within a slot 49 at a location intermediate filter 26 and UV source 24. In this instance, plate 48 is provided with a wave shifting phosphor coating 50 (FIGS. 11 and 12) and is slidably movable within the slot 49 that is formed in housing. The second wavelength conversion means of this latest form of the invention comprises a second conversion plate 54 that is also removably carried by housing 34 within slot 49. Plate 54 is provided with a wave shifting phosphor coating 56 (FIGS. 11 and 12) and is slidably movable within the slot 49. Plate 54 is disposed at a location intermediate plate 48 and filter 26 in the manner shown in the drawings. With the construction shown, either or both plates 48 and 54 can be readily removed from the housing and replaced with alternate plates if desired.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. An apparatus for irradiating an object with ultraviolet radiation comprising:
   (a) a housing having an internal chamber;
   (b) a source of ultraviolet radiation disposed within said chamber for emitting ultraviolet light at a first wavelength;
   (c) filter means carried by said housing at a spaced apart location from said source of ultraviolet radiation for filtering white light from the radiation emitted from said source of ultraviolet radiation;
   (d) a first conversion means removably carried by said housing at allocation intermediate said source of ultraviolet radiation and said filter means for converting the radiation emitted from said source of ultraviolet radiation to radiation at a second wavelength; and
   (e) second conversion means removably carried by said housing at a location intermediate said first conversion means and said filter means for converting the radiation emitted from said source of ultraviolet radiation to radiation at a third wavelength.

2. An apparatus as defined in claim 1 in which said source of ultraviolet radiation emits radiation at a wave length of about 254 nanometers, in which said first conversion means converts the radiation to approximately 300 nanometers and in which said second conversion means converts the radiation to approximately 365 nanometers.

3. An apparatus for irradiating an object with ultraviolet radiation comprising:
   (a) a housing having interconnected top bottom and side walls defining an internal chamber, one of said walls having a first slot;

(b) a source of ultraviolet radiation disposed within said chamber for emitting ultraviolet light at a first wavelength of about 254 nanometers;

(c) filter means carried by said top wall of said housing at a spaced apart location from said source of ultraviolet radiation for filtering white light from the radiation emitted from said source of ultraviolet radiation;

(d) a first conversion means removably carried by said housing at a location intermediate said source of ultraviolet radiation and said filter means for converting the radiation emitted from said source of ultraviolet radiation to radiation at a wavelength of between about 300 nanometers and about 365 nanometers, said first conversion means comprising a conversion plate having a phosphor coating slidably receivable within said slot; and (e) a second conversion means removably carried by said housing at allocation intermediate said first conversion means and said filter means for converting the radiation emitted from said source of ultraviolet radiation to radiation at a third wavelength.

4. An apparatus as defined in claim 3 in which said one of said walls of said housing is provided with a second slot and in which said second conversion means comprises a conversion plate slidably received within said second slot.

* * * * *